United States Patent [19]

Schönberger et al.

[11] 4,174,446

[45] Nov. 13, 1979

[54] PROCESS FOR THE PREPARATION OF $N^1$-(2'-FURANIDYL)-5-FLUORO-URACIL

[75] Inventors: Eva Schönberger, Givatayim; Zabar Sasson, Rehovoth; Uri Michael, Natanya, all of Israel

[73] Assignee: ABIC Ltd., Israel

[21] Appl. No.: 841,023

[22] Filed: Oct. 11, 1977

[30] Foreign Application Priority Data

Oct. 12, 1976 [IL] Israel .................................... 50671

[51] Int. Cl.$^2$ ............................................ C07D 405/04
[52] U.S. Cl. ................................ 544/313; 260/347.8
[58] Field of Search ..................... 260/260; 544/313

[56] References Cited

U.S. PATENT DOCUMENTS 3,912,734   10/1975   Giller et al. .......................... 260/260

*Primary Examiner*—Paul M. Coughlan, Jr.
*Attorney, Agent, or Firm*—Steinberg & Blake

[57] ABSTRACT

The present invention relates to a new process for the preparation of $N^1$-(2'-furanidyl)-5-fluoro-uracil, also called Ftorafur, which is a very important anti-cancer compound. Said process comprises reacting 2,3-dihydrofuran with water in the presence of a catalytic amount of an acidic catalyst at a pH below 2.5, removing excess of unreacted starting materials and reacting the mixture obtained with silylated-5-fluoro-uracil is in the presence of a Friedel Crafts type catalyst uracil in an inert organic solvent. The new process has many advantages in comparison with those used so far.

9 Claims, No Drawings

PROCESS FOR THE PREPARATION OF N¹-(2'-FURANIDYL)-5-FLUORO-URACIL

The present invention relates to a new process for the preparation of N¹-(2'-furanidyl)-5-fluoro-uracil (hereinafter called "Ftorafur").

Ftorafur is a very important anti-cancer compound and has so far been prepared in particular by alkylating 5-fluorouracil or one of its derivatives, e.g., the mercury complex, the silyl or stannyl derivatives. However, so far no entirely satisfactory alkylating agent for the performance of said process has been found.

The most frequently described alkylating agent used for this purpose is 2-chloro-furanidine (e.g., Dokl. Akademia Nauk SSR, 176, 332 (1967); U.S. Pat. No. 3,635,946; and Japanese Patent application 51-008282). However, the use of said chloride has certain drawbacks: 1. No entirely satisfactory process for its preparation is known. All known processes, e.g. those described in H. Gross, Chem. Ber. 95, p. 83 (1962), H. Paulsen et al. Chem.Ber. 108, 2279 (1975) and H. Normant Compt. rend. Ac. Sc. 228 (1949) p. 102, have certain drawbacks, e.g., give low yields, are technically complicated, etc. 2. Some chloro ethers are highly cancerogenic and therefore the use of this volatile compound may be dangerous for people handling it. 3. Both in the preparation of the compound as well as in the final step for the preparation of the Ftorafur, HCl is present which is very undesirable due to the high corrosiveness of that acid.

There are also known some processes in which the 2-chloro-furanidine is replaced by 2-acyloxy, 2-aryloxy, or certain 2-lower alkoxy-furanidines, e.g. Belgian Pat. No. 807,556 and Japanese Pat. No. 50-50 394.

However, it has been found that the use of said compounds is also not entirely satisfactory for the following reasons:

1.a. The manner of their manufacture involves either the use of very undesirable starting materials, e.g. peroxides as described by S. O. Lawesson. Arkiv for Kemi 17, 475 (1961).
   b. or quite complicated working-up procedures in order to separate the compound.
2. Moreover, in the reaction with 5-fluoro-uracil or with 2,4-bis(trialkylsilyl)-5-fluorouracil (hereinafter called "silylated 5-fluoro-uracil") very often undesirable byproducts are obtained, e.g. N¹,N³-bis-(2'-furanidyl-5-fluoro-uracil) - see Japanese Patent Specification 50-50384.
3. Finally, as said starting compounds have to be isolated before they can be further reacted, one cannot use them being formed in situ, i.e. in a "one-pot" process.

It has now been found that the above drawbacks may be overcome to a great extent by performing a one-pot process starting from 2,3-dihydrofuran.

The present invention thus consists in a process for the preparation of Ftorafur which comprises reacting 2,3-dihydrofuran with water in the presence of a catalytic amount of an acidic catalyst at a pH below 2.5 and reacting the mixture obtained with silylated 5-fluorouracil in the presence of a Friedel Crafts type catalyst in an inert organic solvent.

As acidic catalyst there may be used, for example, phosphoric acid, sulfuric acid, sulfonic acids, acid ion exchangers, etc. The preferred pH range is 0–2. The reaction is preferably performed with an excess of 2,3-dihydrofuran. The reaction takes place almost instantaneously and can be performed at room temperature, but is preferably performed at 50–75° C.

The alkylation reaction may be performed at temperatures between −20° to 120° C. However, preferably the reaction is performed at room temperature.

An inert organic solvent in connection with the present invention means a solvent which does not react with any of the reactants and which can dissolve at least one of the starting materials. As suitable solvents there may be mentioned, for example, dioxane, tetrahydrofuran, dihydrofuran and other ethers, acetone, methyl-ethyl-ketone and other ketones, acetonitrils, dimethylformamide, chlorinater hydrocarbons, hydrocarbons, etc.

Suitable Friedel Crafts type catalysts are, inter alia, certain Lewis acids, e.g. $SnCl_4$, $BF_3$ or $TiCl_4$; NaI; etc. Preferably there are utilised up to molar amounts of the catalyst.

The process according to the present invention has many advantages. It proceeds in a very high yield. It can be performed as one-pot process and one of the reactants is water which is an easily available compound and makes the process very economical. Moreover, as far as has been found and been confirmed by the high yields no undesirable side reaction occurs.

It has been found that one of the intermediates obtained in the course of the first reaction step, is a new compound being bis-2-furanidyl ether. This compound can be, if desired, obtained from the reaction mixture by way of distillation.

The present invention will now be illustrated with reference to the accompanying drawings without being limited by them. All temperatures are given in degrees Centigrade.

EXAMPLE 1

2,3-dihydrofuran (16.80 g, 0.240 mole) was slowly added while stirring to a pH=2.0 buffered aqueous solution (1.8 ml, 0.100 mole) while the temperature was kept at 60°–65°. After the addition was completed the reaction mixture was further stirred at 65° for half an hour, cooled to room temperature and the volatile materials were removed by heating to 50° under reduced pressure. 16.50 g of colourless residue were thus obtained. 1.900 g of the crude addition product was added while stirring to a mixture of stannic chloride (0.65 ml; 5.5 m.mole) and anhydrous dioxane (20 ml) followed by silylated 5-fluorouracil (2.740 g; 10.0 m.mole). The reaction mixture was stirred at room temperature for 3 hours and then concentrated under reduced pressure. Thereafter isopropanol (20 ml) was added and the reaction mixture was stirred at room temperature for 10 minutes. After removal of the isopropanol by distillation the resulting crude product was taken up in acetone/petrol-ether and filtered through a silica-gel bed. Ftorafur (1.840 g; m.p. 158°–160°) and unreacted 5-fluorouracil (0.100 g) were thus obtained. Recrystallisation from chlorobenzene (55 ml) gave pure Ftorafur (1.780 g; 96%) m.p. 169°–170°.

EXAMPLE 2

1.600 g crude addition product of water to 2,3-dihydrofuran (prepared as described in Example 1) was added under stirring to a mixture of stannic chloride (0.65 ml; 5.5 m.mole) and anhydrous toluene (20 ml). Immediately afterwards silylated-5-fluorouracil (2.700 g; 10.0 m.mole) was added and the reaction mixture was stirred at room temperature for 3 hours. Isopropanol (5 ml) was added and after 10 minutes stirring at room temperature chloroform was added (25 ml). The resulting mixture was extracted with small portions of a 5% aqueous K$_2$CO$_3$ solution (until PH 7-7.5 was obtained). The aqueous phase was extracted with CHCl$_3$ (4×5 ml). The combined organic layers were dried over MgSO$_4$ and the solvents removed by distillation under reduced pressure. The resulting residue was treated with boiling chlorobenzene (20 ml) filtered hot and the filtrate was concentrated to approximately half of its volume, cooled and diluted with petroleum-ether (10 ml). Ftorafur (1.720 g; 86%) of m.p. 168°-169° was isolated by suction.

EXAMPLE 3

1.600 g crude addition product of water to 2,3-dihydrofuran (prepared as described in Example 1) was added under stirring to a mixture of borontrifluoride-etherate (0.710 g; 5.0 m.mole) and anhydrous dioxane (20 ml) followed by the addition of silylated-5-fluorouracil (2,740 g; 10.0 m.mole). The reaction mixture was stirred for 3 hours at room temperature after which it was worked up as described in Example 1. 0.200 g unreacted 5-fluorouracil and 1.580 g (93%) Ftorafur were isolated.

EXAMPLE 4

2.400 g of crude addition product of water to 2,3-dihydrofuran (prepared as described in Example 1) were added under stirring to a mixture of stannic chloride (0.30 ml; 2.6 m.mole), anhydrous dioxane (25 ml) and 2.740 g (10.0 m.mole) of silylated 5-fluoro-uracil. The reaction mixture was stirred at room temperature for 2 hours after which isopropanol (3 ml) was added and the mixture was stirred for another 5 minutes. The volatile components of the mixture were removed under reduced pressure.

The residual oil was dissolved in chloroform (20 ml) and was stirred for 15 minutes with 15 ml of a 15% aqueous K$_2$CO$_3$ solution. The layers were separated and the organic phase was once more extracted with 3 ml of the 15% aqueous K$_2$CO$_3$ solution. The combined alkaline solutions were acidified to pH 3 and extracted with chloroform (10×5 ml) the combined organic layers were dried over MgSO$_4$ and evaporated to dryness. 1.840 g (92%) of Ftorafur were obtained; m.p. 160°-161°.

EXAMPLE 5

1.600 g of crude addition product of water to 2,3-dihydrofuran (prepared as described in Example 1) were added to a solution of 1.880 g (12.5 m.mole) of sodium iodide in anhydrous acetonitrile (20 ml) and immediately afterwards 2.740 g (10.0 m.mole) of silylated-5-fluorouracil was added. The reaction mixture was brought to reflux and stirred for 4 hours.

The volatile materials were removed under reduced pressure (45°-50°/30 mm Hg). Isopropanol (20 ml) was added to the residual oil and the resulting mixture was stirred for 10 minutes at room temperature after which it was concentrated in vaccuo. The resulting crude product was filtered through silica-gel bed. 0.169 g of unreacted 5-fluorouracil and 1.700 g of Ftorafur were obtained. Recrystallization from chlorobenzene yielded 1.560 g (90%) pure Ftorafur; m.p. 168°-170°.

EXAMPLE 6

2,3-dihydrofuran (52.5 g, 0.750 m.mole) was added while stirring to dilute phosphoric acid (5.4 ml, 0.300 mole; pH=1) while the temperature was kept at 60°-65°. The reaction mixture was further heated to 65° for half an hour. The reaction mixture was cooled and the volatile materials were removed by heating to 50° under reduced pressure. The colourless oily residue (49.0 g) was washed with 3 ml of 25% aqueous K$_2$CO$_3$ solution followed by washing with an aqueous saturated NaCl solution (2×2 ml) dried over MgSO$_4$ and filtered off. The resulting oil (46.0 g) was distilled under reduced pressure through a 1"×" adiabatic column filled with Podbielniak's Heli-Pak 3013 curles (0.050"×0.100"). 19.5 g of a compound being bis-2-furanidyl ether were thus collected; b.p. 93°-95° C./32 mmHg; N.M.R. (in CDCl$_3$); δ=1.90 p.p.m. (complex center); δ=3.53 p.p.m. (complex center) and δ=5.40 p.p.m. (complex center) in ratios 4:2:1 respectively.

I.R. δ neat (microns): 3.40-3.50 (sharp doublet); 6.85-6.95 (sharp doublet); 7.30; 7.50; 8.45; 9.00; 9.30; 9.70; 10.00 (broad); 10.80 (broad); 11.70 (broad).

The most important ions in the mass-spectrum of the compound were at the following mass-units: 41, 57, 71, 87 and 114.

EXAMPLE 7

2,3-dihydrofuran (33.6 g, 0.480 mole) was added while stirring to a suspension of acid washed Amberlite IR-120(H) (0.5 g) in water (3.6 ml, 0.200 mole) while the temperature was kept at 60° C. After the addition was completed the reaction mixture was allowed to cool (30°) and was further stirred for another 12 hours. The pure bis-2-furanidyl ether (11.4 g) was isolated as described in Example 6.

EXAMPLE 8

2,3-dihydrofuran (33.6 g, 0.480 mole) was slowly added while stirring to a pH=2.0 buffered solution (3.6 ml, 0.200 mole) while the temperature was kept at 60°-63°. After the addition was complete the reaction mixture was further heated to 65° for 0.5 hour. The pure bis-2-furanidyl ether (12.5 g) was isolated as described in Example 6.

EXAMPLE 9

Stannic chloride (0.65 ml; 5.5 m.mole) was added while stirring to 20 ml of freshly distilled dioxane. To the above stirred mixture was added bis-2-furanidyl ether (0.948 g, 6.0 m.mole) (prepared as described in Example 6) and thereafter silylated -5-fluorouracil (2.740 g, 10.0 m.mole) was added. The reaction mixture was stirred at room temperature for 3 hours and then it was concentrated under reduced pressure (50°-55° C./30 mmHg). Isopropanol (20 ml) was then added to the residue and after stirring for few minutes at room temperature the isopropanol was removed by distillation in vaccuo. The crude reaction mixture was applied on a silicagel column. Ftorafur (1,490 g, m.p. 159°-160° C.) was first eluted by 4:6 mixture of acetone:petroleum-ether (b.p. 40°-60°) and was followed by 5-fluorouracil (0.320 g). Recrystallization from isopropanol (35 ml) yielded pure Ftorafur (1.420 g, 94%) m.p. 169°-170°.

We claim:
1. Method of producing N$^1$-(2'-furanidyl)-5-fluorouracil which comprises reacting 2,3-dihydrofuran with water in the presence of a catalytic amount of an acidic catalyst at a pH below 2.5, thereby forming a reaction mixture including unreacted starting materials, removing the unreacted starting materials and reacting the remaining reaction mixture with silylated-5-fluorouracil in the presence of a Friedel Crafts catalyst in an inert organic solvent thus forming the $N^1$-(2'-furanidyl)-5-fluorouracil in high yield.

2. Method according to claim 1 wherein the acidic catalyst is selected from the group consisting of phosphoric acid, sulfuric acid, and sulfonic acids.

3. Method according to claim 1 wherein the first step is performed at a pH 0–2.

4. Method according to claim 1, wherein the first step is performed with 2,3-dihydrofuran in excess of the stoichiometric.

5. Method according to claim 1 wherein the Friedel Crafts catalyst is a Lewis acid.

6. Method according to claim 5, wherein the Friedel Crafts catalyst is selected from the group consisting of $SnCl_4$, $BF_3$ and $TiCl_4$.

7. Method according to claim 1 wherein the Friedel Crafts catalyst is NaI.

8. Method according to claim 1 wherein the inert solvent is selected from the group consisting of dioxane, tetrahydrofuran, dihydrofuran, acetone, methylethylketone, acetonitrile, dimethylformamide, chlorinated hydrocarbons and hydrocarbons.

9. Method according to claim 1 wherein both reaction steps are performed at room temperature.

* * * * *